(12) United States Patent
Thornton

(10) Patent No.: US 8,075,183 B2
(45) Date of Patent: Dec. 13, 2011

(54) METHOD OF EVALUATING THE RESOLUTION OF A VOLUMETRIC IMAGING SYSTEM AND IMAGE PHANTOM USED DURING THE RESOLUTION EVALUATION

(75) Inventor: Michael M. Thornton, London (CA)

(73) Assignee: Volumetrics Medical Corp., London, Ontario (CA)

( * ) Notice: Subject to any disclaimer, the term of this patent is extended or adjusted under 35 U.S.C. 154(b) by 709 days.

(21) Appl. No.: 11/917,855

(22) PCT Filed: Jun. 19, 2006

(86) PCT No.: PCT/CA2006/001010
§ 371 (c)(1),
(2), (4) Date: Jul. 22, 2008

(87) PCT Pub. No.: WO2006/133574
PCT Pub. Date: Dec. 21, 2006

(65) Prior Publication Data
US 2008/0317198 A1    Dec. 25, 2008

Related U.S. Application Data

(60) Provisional application No. 60/691,292, filed on Jun. 17, 2005.

(51) Int. Cl.
*G01D 18/00* (2006.01)
(52) U.S. Cl. .......................... 378/207; 378/18
(58) Field of Classification Search .................. 378/18, 378/204, 207, 62
See application file for complete search history.

(56) References Cited

U.S. PATENT DOCUMENTS

| 2003/0007601 A1 | 1/2003 | Jaffray et al. |
| 2003/0227999 A1* | 12/2003 | Cresens .................. 378/207 |
| 2007/0071176 A1* | 3/2007 | Main et al. .............. 378/207 |

OTHER PUBLICATIONS

Seifert et al. (2002) "Resolving Power of 3D X-ray Mocrotomography Systems" Medical Imaging 2002: Physics of Medical Imaging —Proceedings of SPIE vol. 4682, pp. 407-413.*
Seifert, et al.: "Resolving Power of 3D X-ray Microtomography Systems", p. 407-413, vol. 4682, Medical Imaging 2002, Proceedings of SPIE, 2002.
Reimann, et al.: "Direct Measurement of Resolution in Volumetric Imaging Systems", pp. 1784-1787, vol. 4, Nuclear Science Symposium and Medical Imaging Conference, 1994.

* cited by examiner

*Primary Examiner* — Courtney Thomas
(74) *Attorney, Agent, or Firm* — Baker & Daniels LLP

(57) ABSTRACT

A method for evaluating the spatial resolution of a volumetric medical imaging system comprises imaging an image phantom including a sphere surrounded by a uniform medium. The image phantom is imaged and the resulting volumetric data set is used to generate an edge response function in three dimensions. Differentiating the edge response function produces a plane spread function. The method simultaneously measures the spatial resolution in all directions, providing a bulk measurement resolution. Alternatively, the edge response function may be assembled in a manner so as to independently measure the axial and trans-axial resolution of the volumetric imaging system.

29 Claims, 6 Drawing Sheets

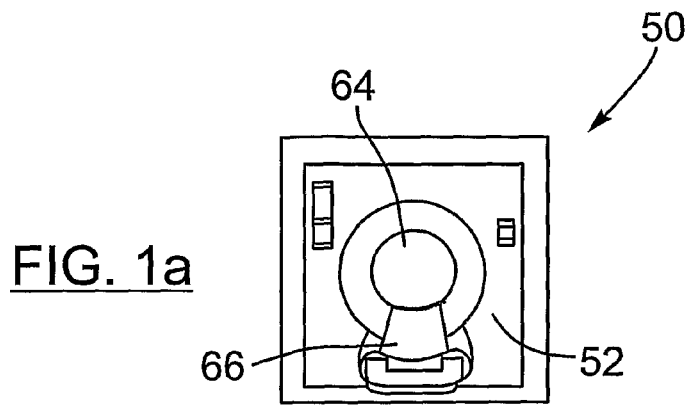
FIG. 1a
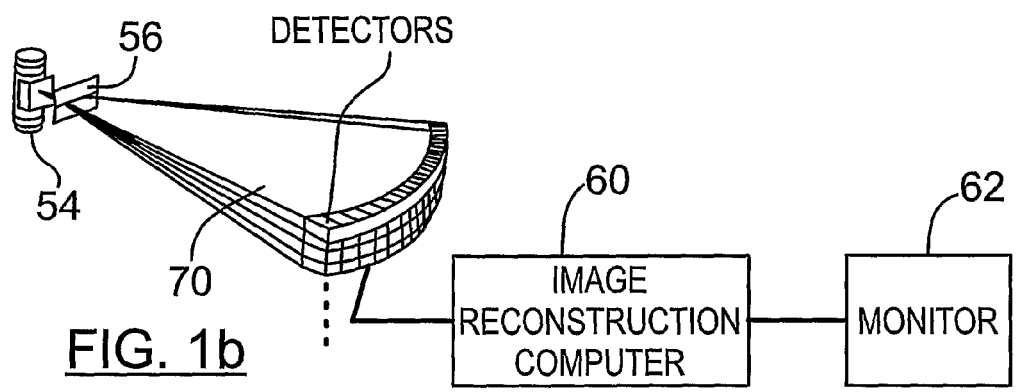
FIG. 1b
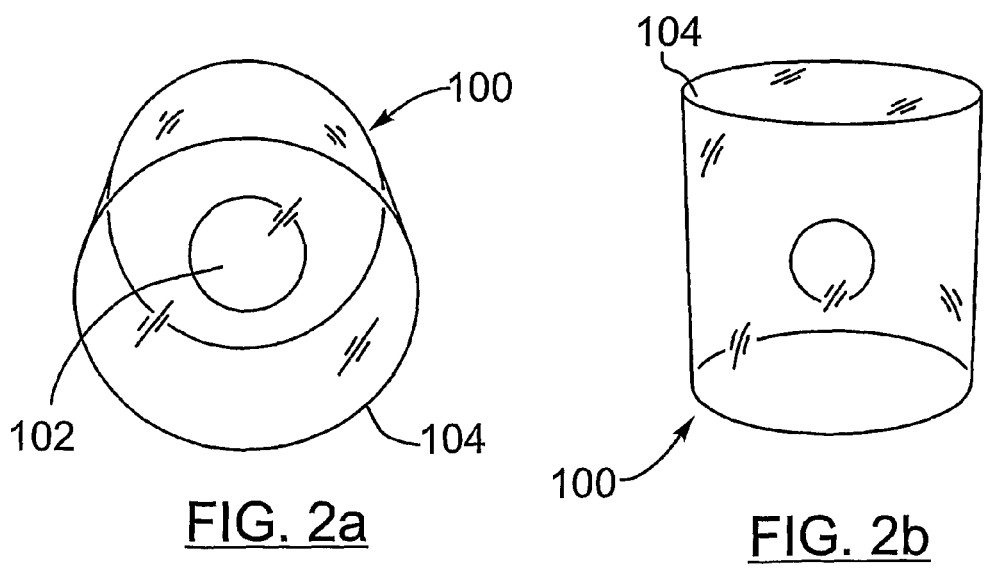
FIG. 2a
FIG. 2b

METHOD OF EVALUATING THE RESOLUTION OF A VOLUMETRIC IMAGING SYSTEM AND IMAGE PHANTOM USED DURING THE RESOLUTION EVALUATION

FIELD OF THE INVENTION

The present invention relates generally to medical imaging, and more particularly to a method of evaluating the resolution of a volumetric imaging system and image phantom used during resolution evaluation.

BACKGROUND OF THE INVENTION

The evolution of mathematical concepts in tomographic reconstruction and technological advances in instrumentation, and computing in the late 1960s led to the development of x-ray computed tomography (CT). Single-slice, first generation CT scanners became available commercially in the early 1970s for clinical applications for diagnostic imaging of the head. These first generation CT scanners consisted of a pencil beam geometry and a single detector utilizing a translate and rotate acquisition geometry which required several minutes to produce a single cross-sectional image slice (tomogram) through the skull. The publication entitled "Computerized transverse axial scanning (tomography)" authored by Hounsfield, British Journal of Radiology, 1973 December; 46 (552): 1016-22 discloses such a first generation CT scanner.

The impact of CT scanning technology was significant and led to the rapid development of new systems which employed larger x-ray beams and more detectors in order to decrease scan time and increase the area of scan coverage. By the early 1980s, clinical CT scanners could acquire transverse (trans-axial), single cross-sectional images through any part of the human anatomy in a matter of seconds. By the early 1990s, clinical CT scanners combined bed patient motion in the axial direction with gantry rotation speeds in the order of one (1) second per revolution to generate so-called helical data sets. These CT scanners routinely generated stacks of two dimensional (2-D) image slices representing the three dimensional (3-D) volume of the anatomy being scanned. The discrete elements forming the 3-D volume are commonly referred to as voxels. The availability of advanced computing and visualization equipment allowed physicians and scientists to arbitrarily view image slice data through the scanned 3-D volume of tissue.

By the late 1990s, CT scanners were developed with multiple rows of detectors and larger x-ray beam coverage (extending several slices axially), which further decreased the scanning time for imaging large volumes of anatomy. In 2004, CT scanners generating sixty-four (64) slices per gantry rotation became commercially available. In 2005, CT scanners became available that acquire 3-D data sets with the so-called cone-beam geometry (divergent x-ray beam fully extending across the trans-axial direction and covering many slices axially) in a matter of seconds. The 3-D voxel data set generated by these CT scanners is typically reformatted and viewed using a number of display techniques, i.e. multi-planar reformatting, maximum/minimum intensity projection, and volume rendering.

In addition to CT scanning, other volume imaging modalities such as for example, magnetic resonance, ultrasound, and nuclear/PET imaging, have been developed that generate 3-D data sets.

Quantifying the spatial resolution, resolving power, or detail detectability of an imaging system has always been of significant interest and utility, particularly in medical imaging systems. Standard methods of assessing resolution include line-pair or spoked phantoms (test objects) which contain high contrast structures with varying spatial frequencies. These phantoms are 2-D in nature and typically, imaging system performance is evaluated through the visual inspection of phantom image data where the highest spatial frequency for which structures can be discriminated (resolved) indicates the limiting spatial resolution. Line-pair phantoms assess resolution in one dimension only and may be rotated and re-imaged to assess resolution in the axial and trans-axial directions.

In 1976, a method by which a continuous set of spatial frequencies could be examined simultaneously, to examine CT scanner spatial resolution performance was proposed and is described in the publication entitled "The line spread function and modulation transfer function of a computed tomographic scanner" authored by Judy, Medical Physics, 1976, July-August; 3(4): 233-6. The disclosed method involves imaging a high contrast slanted edge trans-axially. The image slice data provides the edge response function (ERF), which in turn provides the response of the CT scanner to a step function. Differentiating the ERF generates a point spread function (PSF) and thus, the response of the CT scanner to an impulse (delta) function. Since the impulse function contains all frequencies, this means that the response of the CT scanner to all spatial frequencies may be assessed, in one dimension, simultaneously, by imaging the slanted edge.

The 'slanting' of the edge in a 2-D image allows for oversampling, thereby overcoming the limitations of discrete sampling inherent to digital data sets. The edge may be rotated in the scanning field of the CT scanner to measure the resolution in the 'left-right' and 'anterior-posterior' directions of trans-axial images. The edge may be rotated again to measure axial resolution.

Assessment of resolution in a CT scanner for quality control purposes has typically been done using a bar pattern phantom with a series of stacked plates aligned with the axis of the CT scanner. While quantitative modulated transfer function (MTF) measures of bar pattern data have been reported, most quantitative measures have been made with wires, thin plates, or the surface of a block. In all cases, the phantoms are aligned with the axis of the CT scanner and the data from a transverse slice is analyzed using traditional methods for assessing the MTF from a point spread function (PSF), line spread function (LSF), or edge spread function (ESF). For these methods, the two-dimensional image data is analyzed using traditional radiographic methods that relate the PSF, LSF, and ESF to the MTF.

The importance of resolution measurements is driven by the interdependent relationship between image quality (noise), resolution, and dose. A novel method for quantifying spatial resolution in a volume micro-CT scanner is described in the publication entitled "Resolving Power of 3D Microtomography Systems" authored by Seifert and Flynn, Medical Imaging 2002, Proceedings of SPIE Vol. 4682 (2002):407-413). The method involves imaging a sphere of uniform material composition immersed in a homogeneous media. The sphere represents a '3-D edge'. The sphere and surrounding media are imaged, and the voxel intensity for each voxel, in the resulting volume data set, is plotted as a function of distance from the center of the sphere. This plot represents the ERF in all directions and is referred to as the surface spread function (SSF). The surface spread function is differentiated to produce the equivalent of the PSF, which is subsequently Fourier transformed to produce the modulated transfer function (MTF) for the micro-CT scanner.

For modern multislice CT (MSCT) scanners, which routinely produce three dimensional volumetric data sets with nearly isotropic resolution, methods that can assess the MTF as a function of direction in three dimensions (3D) are needed.

It is therefore an object of the present invention to provide a novel method of evaluating the resolution of a volumetric imaging system and image phantom used during resolution evaluation.

SUMMARY OF THE INVENTION

Accordingly, in one aspect there is provided a method of evaluating the spatial resolution of volumetric imaging system, comprising:

scanning an image phantom comprising a sphere formed of generally uniform material surrounded by a generally uniform medium with a divergent beam and generating volumetric image data of said image phantom;

reconstructing a volumetric image of said image phantom; and generating a multi-directional edge response function from said volumetric image of image phantom.

According to another aspect there is provided a method of evaluating the axial and trans-axial resolution of a volumetric imaging system, comprising:

placing a high contrast sphere in a uniform medium within the field of view of said volumetric imaging system;

creating a conic region which is generated by rotating a ray, centered at the sphere centroid, about the axial directional ray of the scanning geometry, such that the cone angle is acute;

forming the edge response function using voxel data lying inside the conic region to quantify the resolution of the volumetric imaging system in the axial direction; and forming the edge response function using voxel data lying outside of the conic section to quantify the resolution of the volumetric imaging system in the trans-axial direction.

According to yet another aspect there is provided a method of displaying the inherent image spatial resolution during data visualization comprising:

quantifying the axial and trans-axial resolution for a scanning protocol for a given scanner;

determining the directionally dependant resolution of the scanner during display of an image; and presenting a graphical representation of the directionally dependant resolution corresponding to the orientation of the image being viewed.

According to still yet another aspect there is provided an image phantom comprising:

a sphere formed of generally uniform material; and a medium of generally uniform material surrounding said sphere.

The present invention provides advantages in that the SSF and resulting PISF are vastly over-sampled as compared to standard techniques that employ a thin wire to generate an LSF. In addition, the signal-to-noise ratio is higher for the characteristic blur function as compared to equinity measurements for a thin wire resulting in higher precision. Furthermore, blur is characterized in all directions simultaneously and therefore allows directionally dependent resolution to be measured using a single scan data set. Also, no mechanical alignment is necessary nor is any post-processing to correct for image phantom orientation.

BRIEF DESCRIPTION OF THE DRAWINGS

Embodiments will now be described more fully with reference to the accompanying drawings in which:

FIGS. 1a and 1b show a multislice CT (MSCT) scanner;

FIGS. 2a and 2b show an imaging phantom comprising a sphere centrally positioned within a cylinder;

DETAILED DESCRIPTION OF THE EMBODIMENTS

Figure 3:
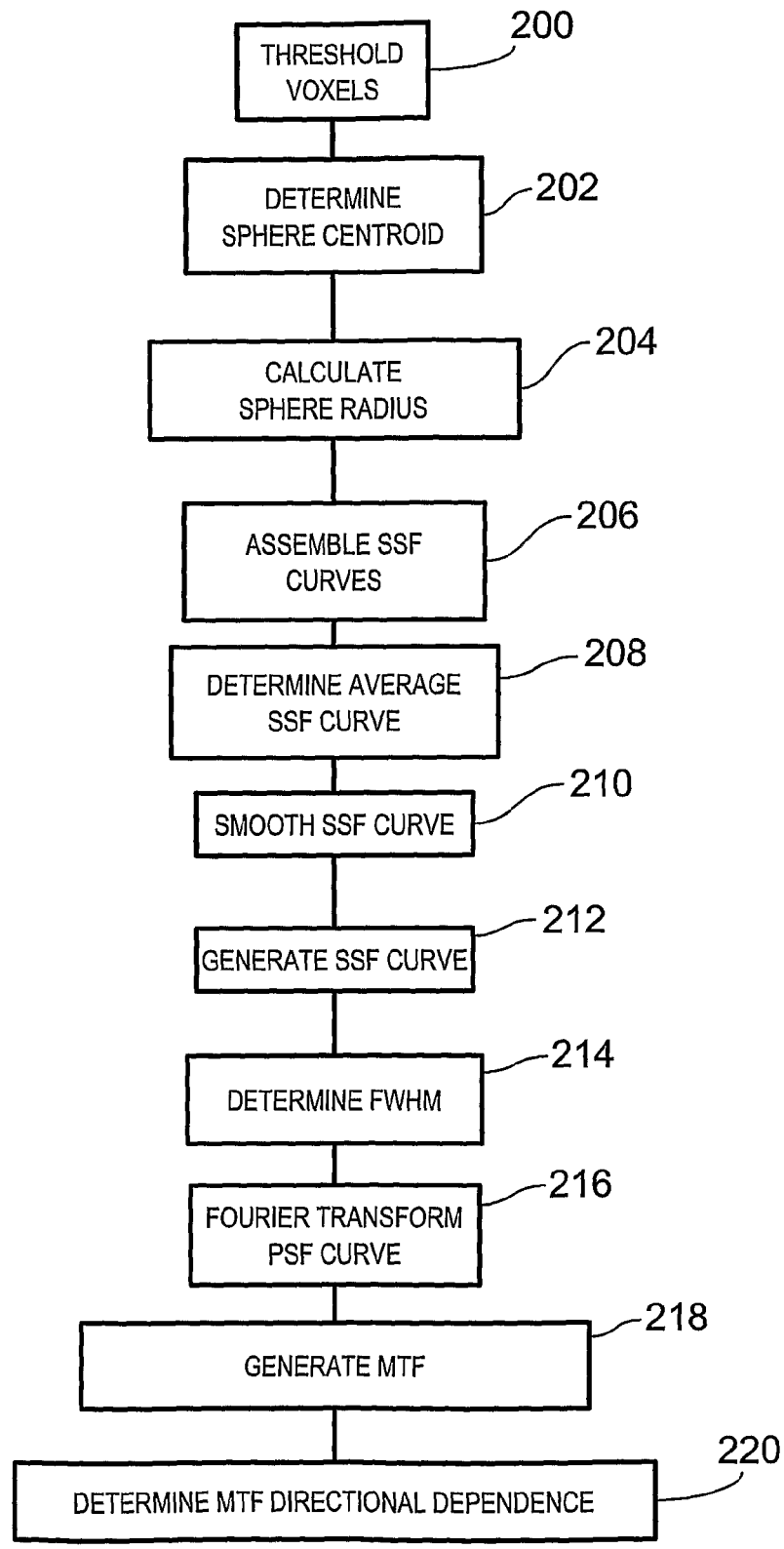
FIG. 3 is a flowchart showing the steps performed during processing of volumetric image data of the image data to evaluate the resolution of the MSCT scanner.

A method for evaluating or quantifying resolution of a volumetric imaging system such as for example, a multislice CT (MSCT) scanner is disclosed. During the method, volumetric image data of an image phantom is acquired and processed to determine the modulation transfer function (MTS) of the volumetric imaging system as well as the directional dependence of the MTS. The image phantom provides for the simultaneous measurement of volumetric imaging system resolution in virtually all directions as well as the independent measure of resolution in any direction, without the need for repositioning or alignment of the image phantom. During display of reconstructed volumetric images, a graphical object or icon is also displayed identifying the resolution of the volumetric imaging system in the direction of the volumetric image being viewed. Further specifics will now be described with reference to FIGS. 1 to 3.

FIGS. 1a and 1b show an MSCT scanner generally identified by reference numeral 50. As is well known to those of skill in the art, MSCT scanner 50 comprises a gantry 52 accommodating an x-ray source 54 and collimator 56. Rows of detectors 58 are also accommodated by the gantry 52 diametrically opposite the x-ray source 54 and collimator 56. In this embodiment, the gantry 52 accommodates at least thirty-two (32) rows of detectors 58. An image reconstruction computer 60 communicates with the detectors 58 and reconstructs volumetric images from the volumetric image data output by the detectors 58. A monitor 62 communicates with the image reconstruction computer 60 and displays the generated volumetric images.

The gantry 52 has a central opening 64 into which a patient supporting table 66 extends. The gantry 52 is rotatable about the table 66 and tiltable with respect to the table 66 to allow a full compliment of images of a patient or object supported on the table 66 to be acquired.

In order to evaluate the resolution of the MSCT scanner 50, the MSCT scanner 50 is conditioned to scan an image phantom using the selected scanning protocol. During scanning, the x-ray source 54 outputs an x-ray beam 70 that is fanned by collimator 56. The fanned x-ray beam 70, after passing through the image phantom, impinges on the multiple rows of detectors 58. In response, the detectors 58 output volumetric image data (voxels) that are received by the image reconstruction computer 60. At the same time, the gantry 52 is rotated about the table 66 and the table 66 is translated relative to the opening 64 in the gantry 52 so that the image phantom is fully scanned. The gantry 52 in this case is rotated about the table 66 at a rate less than or equal to one (1) rotation per second. The image reconstruction computer 60 in turn processes the volume image data received from the detectors 58 thereby to reconstruct volumetric images of the image phantom that are displayed on monitor 62.

As mentioned above, the configuration of the image phantom is such so as to allow the resolution of the MSCT scanner 50 to be evaluated. Turning now to FIGS. 2a and 2b, the image phantom is shown and is generally identified by reference numeral 100. As can be seen, image phantom 100 comprises a sphere 102 generally centrally positioned within a cylinder or puck 104. The sphere 102 and cylinder 104 are formed of generally uniform materials having low atomic numbers to help produce volumetric image data sets that are free from x-ray beam hardening artifacts. In this embodiment, sphere 102 is formed of Teflon® which has an effective atomic number equal to 8.47 and a mean value of 900 Houndsfield units (HU). As will be appreciated the effective atomic number of Teflon® is very close to that of soft tissue. The increased HU mean value of the sphere 102 as compared to soft tissue is primarily due to its density. The cylinder 104 is formed of curable liquid silicone having a mean value equal to 190 HU. The attenuation coefficient of the sphere 102 is at least three times greater than the attenuation coefficient of the cylinder 104. the sphere contrasts the cylinder sufficiently to allow the sphere to be differential from the cylinder in acquired volumetric images.

The diameter of the sphere 102 is selected to be at least three times greater than the voxel spacing of the volumetric images of the image phantom 100. In this embodiment, the sphere 102 has a diameter equal to 0.5 inches. The cylinder 104 has a diameter equal to 4 inches and a height equal to 4 inches. As will be appreciated, the shape of the sphere 102 has a curvature that emulates biological structures making it particularly suited to MSCT scanner resolution evaluation. Also, the symmetry of the sphere 102 permits measurement of blur in virtually any direction without requiring special alignment as will be described.

During formation of the image phantom 100, the image phantom 100 is molded in a two-part procedure under low pressure to position centrally and immerse the sphere 102 within the cylinder 104 and to ensure the cylinder 104 is free of entrapped air bubbles.

In order to evaluate the resolution of the MSCT scanner 50, the reconstructed volumetric image data is processed to generate a surface spread function (SSF) representing the edge response function for the MSCT scanner 50 that is used to quantify the resolution of the MSCT scanner in all directions. The SSF is a graphical plot which maps the intensity value of each voxel as a function of the voxel's distance from the centroid of the sphere 102. The SSF is then differentiated to produce a plane spread function (PISF). The results are then interpreted using full width at half maximum (FWHM), and Fourier transforming to generate a modulation transfer function (MTF). The FWHM represents the apparent width (blur) in the image space of an infinitely thin sheet while the MTF quantifies how spatial frequencies are modulated as they pass through the MSCT scanner 50.

Turning now to FIG. 3, the processing of reconstructed volumetric image data in order to evaluate the resolution of the MSCT scanner 50 will be further described. Initially, the volumetric image data of the image phantom 100 is thresholded into voxels interior to and exterior to the sphere 102, by comparing the gray-level values of the voxels with a threshold value that is intermediate the mean interior and exterior gray-level values of the sphere (step 200). Voxels within the sphere 102 are set to an intensity of one, while voxels outside of the sphere 102 are set to an intensity of zero. Following the thresholding procedure, the voxels within the sphere 102 are processed to calculate the centre of mass of the sphere 102 thereby to determine the centroid of the sphere 102 (step 202). The thresholded volumetric image data is also used to calculate the radius of the sphere 102 by determining the extent of the voxels that are set to unity intensity (step 204). The original unthresholded volumetric image data is then used for the remainder of the analysis.

All voxels a distance greater than eight voxel dimensions from the centroid of the sphere 102 and less than three sphere radii from the sphere centroid are used to assemble the surface spread function (SSF) (step 206). The distance of each of these voxels from the sphere centroid is calculated and the distances are placed into the bins of a histogram one tenth the size of the in-plane resolution. The gray-level values of the voxels are accumulated into one set of bins, and the numbers of voxels at given distances are accumulated into another set of bins. Following this procedure, the accumulated gray-level values are divided by the numbers of voxels in the bins to yield an averaged SSF curve (step 208).

A bspline algorithm using cubic basis functions is used to smooth the averaged SSF curve (step 210). Control points are placed at four times the spacing in the averaged SSF curve (still two and a half times the original in-plane image resolution). The smoothed SSF curve is evaluated from the bspline coefficients at the original coordinates, preserving the spacing at one tenth the original in-plane resolution.

The binned, smoothed SSF curve is digitally differentiated by evaluating the difference between successive SSF values thereby to yield a resulting PISF curve (step 212). The full width at half maximum (FWHM) is then determined from the PISF curve (step 214).

The PISF curve is Fourier transformed using an algorithm adapted from the realfi routine from Numerical Recipes (step 216). This algorithm replaces a real-valued function with the positive-frequency half of its complex Fourier transform. For this algorithm, the data must be radix 2, so the PISF curve data is zero padded to increase the array size to the nearest power of two prior to Fourier transforming. The magnitude of the resulting complex array is calculated, and normalized to unity at zero spatial frequency thereby to yield the MTF (step 218). The 10% MTF represents the limiting spatial resolution of the MSCT scanner 50.

The directional dependence of the MTF is then evaluated by approximating the MTF along the positive and negative directions of each coordinate axis, in other words, by evaluating six independent MTF curves (step 220). In particular, axial and trans-axial resolution of the MSCT scanner is evaluated.

Figure 4:
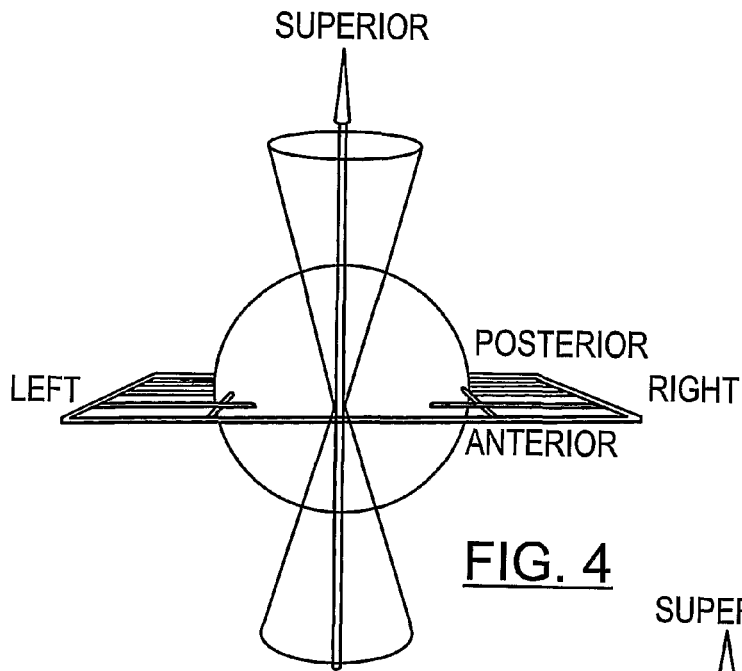
FIG. 4 shows the cores from which voxels are recruited to assemble SSF curves during axial resolution evaluation.

During axial resolution evaluation, a ray is drawn from the sphere centroid subtending 30 degrees to the positive axial direction (superior) rotated to produce a cone. Similarly, a second cone is drawn subtending 30 degrees to the negative axial direction (inferior). The voxels within these two cones are used to assemble the SSF curves in the positive and negative axial directions, respectively. FIG. 4 shows the cones from which the voxels are recruited to assemble the SSF curves. The procedure for assembling the SSF curves is the same as that described above, with the exception that the contribution from each voxel is weighted by the squared ratio of its axial coordinate to its distance from the sphere centroid, thereby assigning increased weight to voxels located closer to the axial axis.

Figure 5A:
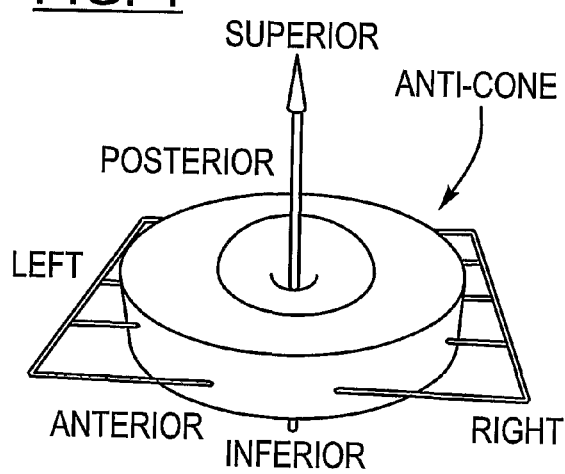
FIG. 5a shows an anti-cone from which voxels are recruited to assemble SSF curves during trans-axial resolution evaluation.
Figure 5B:
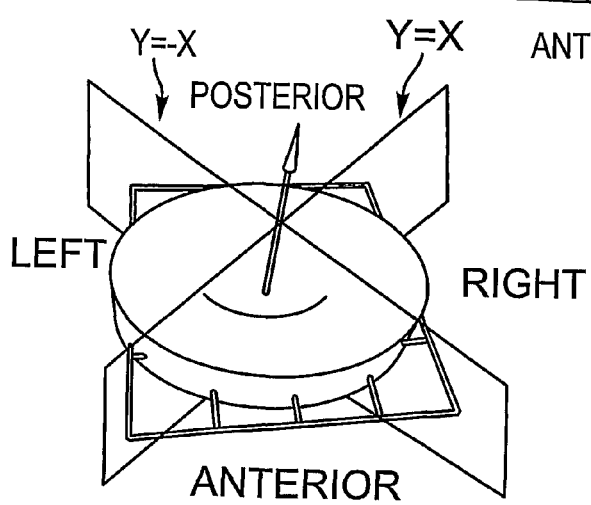
FIG. 5b shows x=y and y=−x planes that bisect the anti-cones.

For trans-axial resolution evaluation, a ray is drawn from the centroid subtending 60 degrees to the positive axial direction rotated to produce a cone. However, in this case the anti-cone outside this cone and above the transverse plane is used. The union of the anti-cone and the similar anti-cone below the transverse plane is further subdivided into four quadrants defined by the planes x=y and y=−x. The voxels within these four quadrants are used to assemble the SSF curves in the positive and negative x (right-left) and y (anterior-posterior) directions. The anti-cone from which voxels are recruited to assemble the SSF curves is shown as the shaded volume in the left side of FIG. 5. The x=y and y=−x planes that bisect the anti-cone are shown in the right side of FIG. 5. Once again, the contribution from each voxel is weighted by the squared ratio of its coordinate along the relevant axis to its distance from the sphere centroid, thereby assigning greater weight to voxels located closer to the axis in question.

Following the assembly of the six independent SSF curves, the procedure of smoothing the SSF curves with bsplines, differentiating the smoothed SSF curves to obtain the PISF curves, and Fourier transforming to obtain the MTF curves, is the same as that described above.

The axial and trans-axial resolutions evaluated for the MSCT scanner are recorded. During subsequent imaging of patients using the MSCT scanner, the recorded resolutions are used to update a graphical icon presented on the monitor 62 with the displayed volumetric image so that the resolution of the MSCT scanner in the particular direction being viewed is also displayed. In this manner, variations in image quality resulting from changes in MSCT scanner resolution can be visually determined inhibiting such variations from being wrongly interpreted as image artifacts.

Imaging of the image phantom 100 may be repeated by varying the position of the image phantom radially, and axially, to evaluate the resolution of the volumetric imaging system throughout the scan field. For example, the image phantom may be placed at the middle of the scan field, 20% of the radius, 50% and 80% of the radius to evaluate the spatial resolution as a function of radial position within the scan field. In addition, the resolution loss due to table motion in helical scans may be quantified by scanning the image phantom using a helical scanning protocol.

Figure 9:
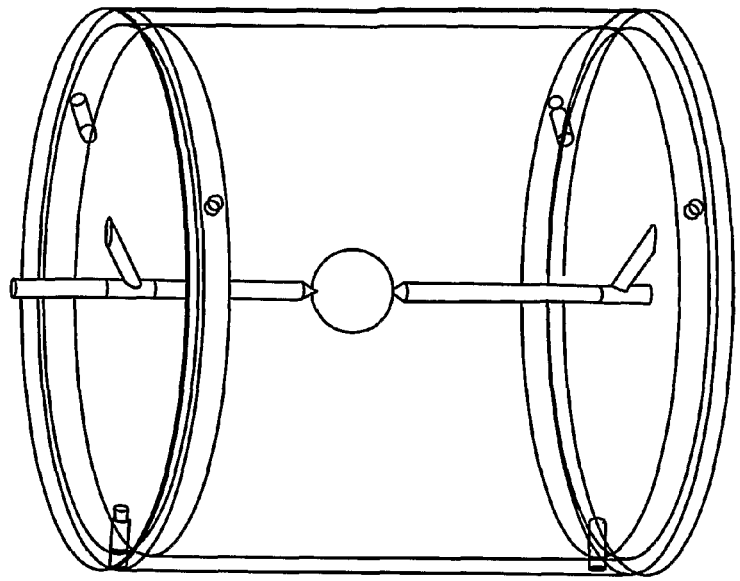
FIG. 9 is another embodiment of an image phantom.
Figure 10:
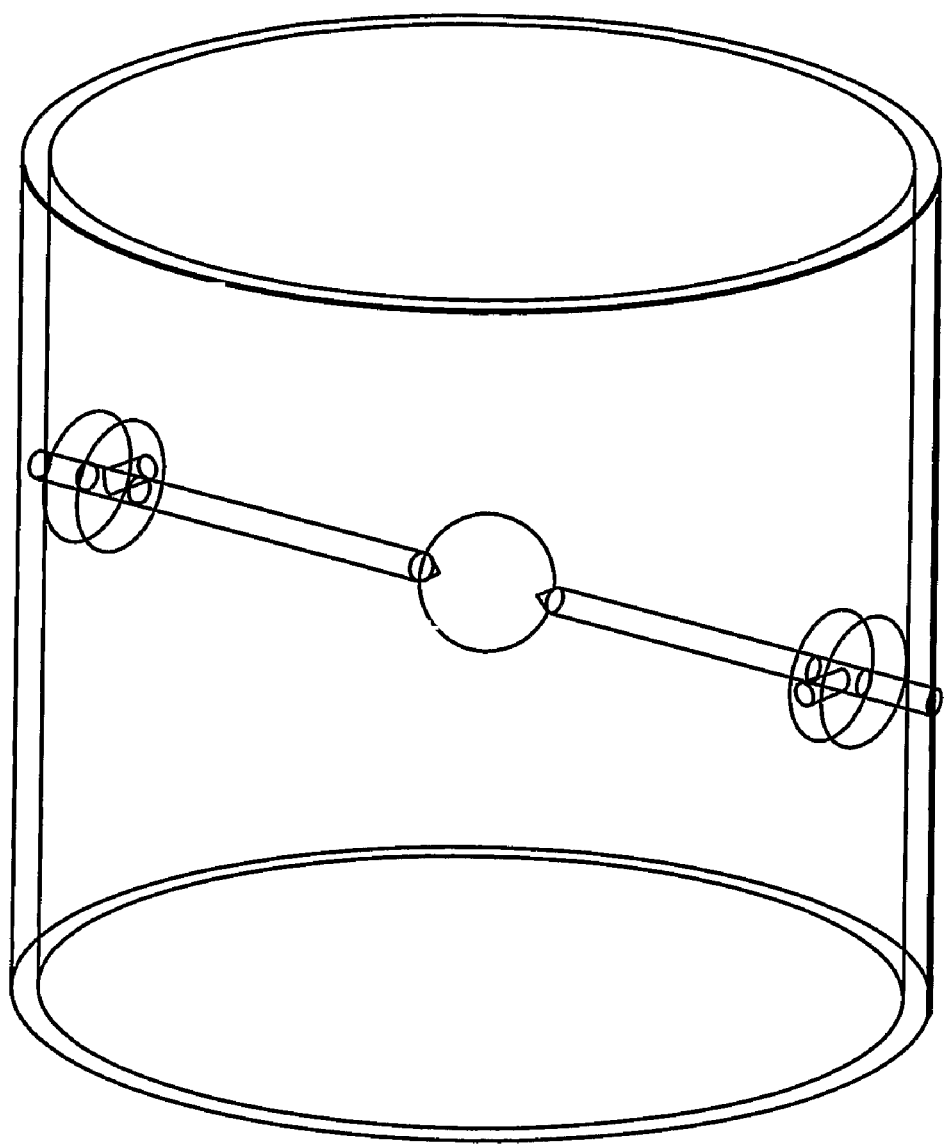
FIG. 10 is yet another embodiment of an image phantom.

Turning now to FIGS. 9 and 10, alternative embodiments of an image phantom are shown. In these embodiments, the spheres are suspended in one dimension within cylindrical contours by support structures. The spheres in these cases may be surrounded by air or the volume encompassed by the containers may be evacuated to create a vacuum therein.

EXAMPLES

Volumetric scans of the image phantom 100 were acquired with two commercially available clinical volumetric CT scanners, namely a General Electric Healthcare Lightspeed VCT (GE VCT) and the Siemens Medical Systems SOMATOM Sensation 64-slice (SMS 64). Scanning parameters were matched as closely as possible for the two CT scanners, and reflect typical protocols used in 30 clinical practice at HFHS. The spiral scanning protocol used to acquire the volumetric scans is shown in Table 1 below.

TABLE 1

| Scan Parameter | Value | Notes |
|---|---|---|
| Tube voltage | 120 kVp | |
| Tube current | 200 mA | |
| Axial FOV | 100 mm | |
| Recon diameter | 200 mm | |
| Gantry speed | 1.0 sec | |
| Collimation | 20 mm | no collimation for the Sensation 64 |
| Recon filter | standard | H40 medium, for the Sensation 64 |
| Slice thickness | 0.625 mm | 0.6 mm, for the Sensation 64 |
| In-plane voxel size | 0.39 1 mm | |

During scanning, the image phantom 100 was positioned such that sphere 102 was located approximately at iso-centre. Volumetric scans were acquired using the spiral scanning protocol of Table 1 with a table speed of 20 mm/sec and a pitch of 1.0 for three (3) sphere diameters, namely 0.5 inches, 1 inch and 1.5 inches in order to investigate the influence of sphere diameter on measured resolution. A larger sphere diameter is desirable due to increased over-sampling but should be constrained to a size that does not cause significant x-ray beam hardening which would distort the measurement of spatial resolution Five (5) additional scans of the image phantom 100 having a 1 inch sphere diameter were acquired with the GE VCT to determine the precision of the measurement technique. To study Azimuthal blur, the image phantom 100 was positioned at the periphery of the scan field of view with the sphere 102 located at approximately 180 mm from iso-centre in the right-left direction. Volumetric image data was acquired with gantry speeds of 1.0 and 0.4 seconds per rotation.

The diameter of the spheres 102 was measured at 8 points, along 6 lines of longitude, to assess sphericity. The variation in diameter was found to be less than 25 gm, for a given sphere. Visual inspection of the clear silicone cylinders 104 did not show any inclusions of air.

Reconstructed images of the image phantom were copied from the CT scanner console in the slice based DICOM file format and converted into a single volume data file. Voxel values from the single volume data set were used to assemble the SSF in order to compute the FWHM and 10% MTF for the scanning modes which were investigated.

Figure 6:
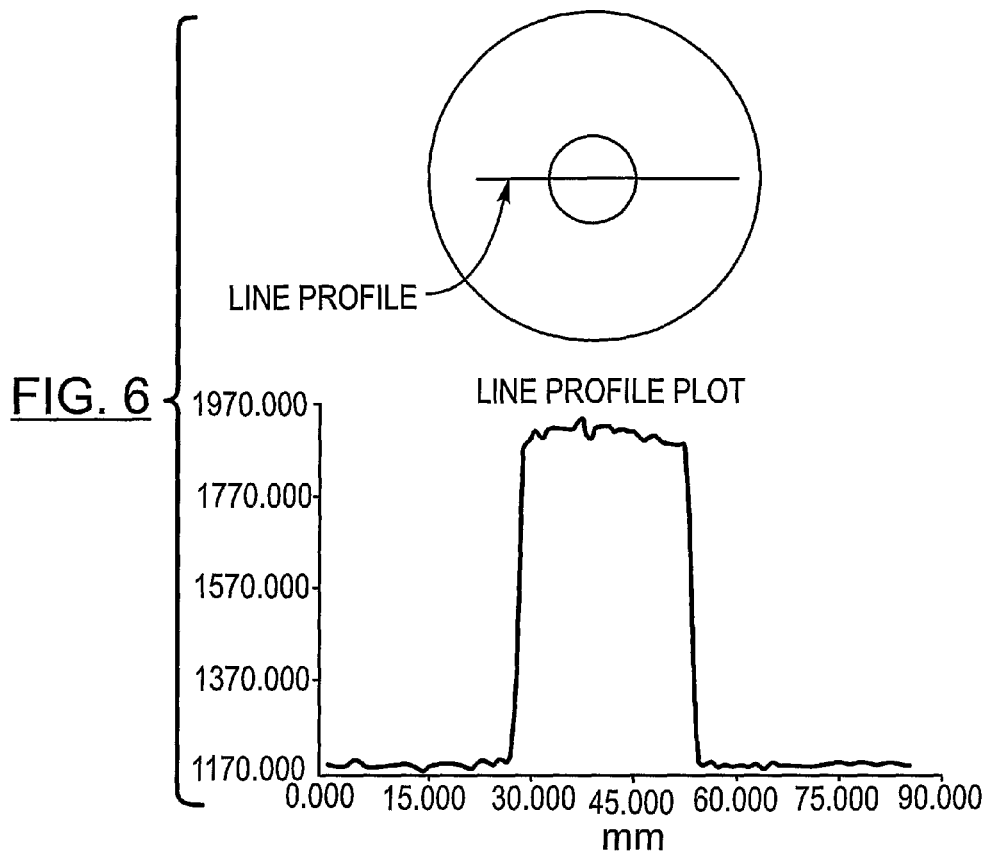
FIG. 6 shows an image slice through a volumetric image of the image phantom and a profile line plot taken through the image slice.
Figure 7:
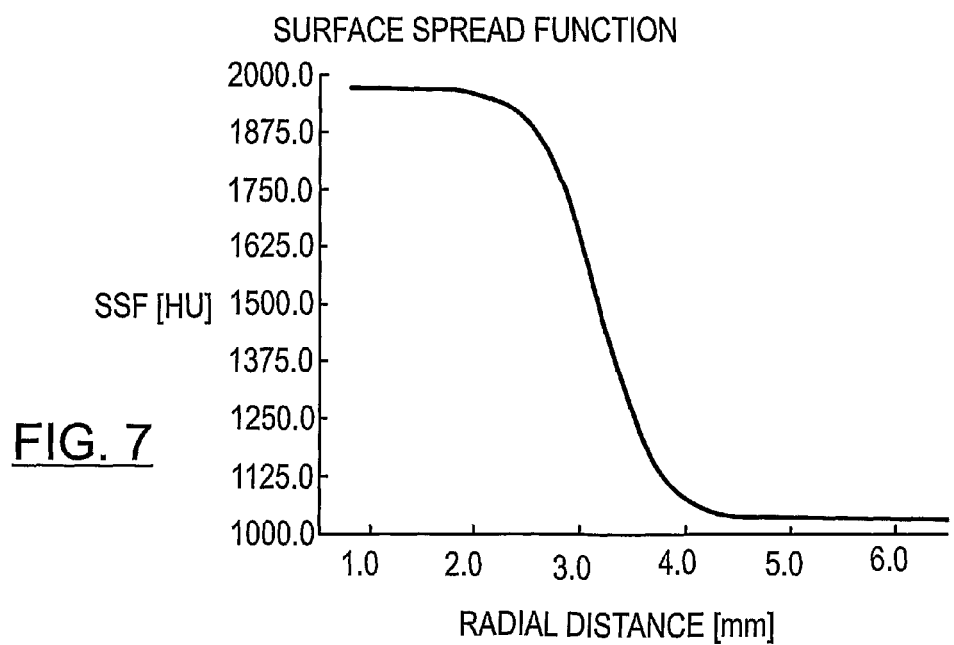
FIG. 7 is a resultant SSF curve derived from the data of the profile line plot of FIG. 6.
Figure 8:
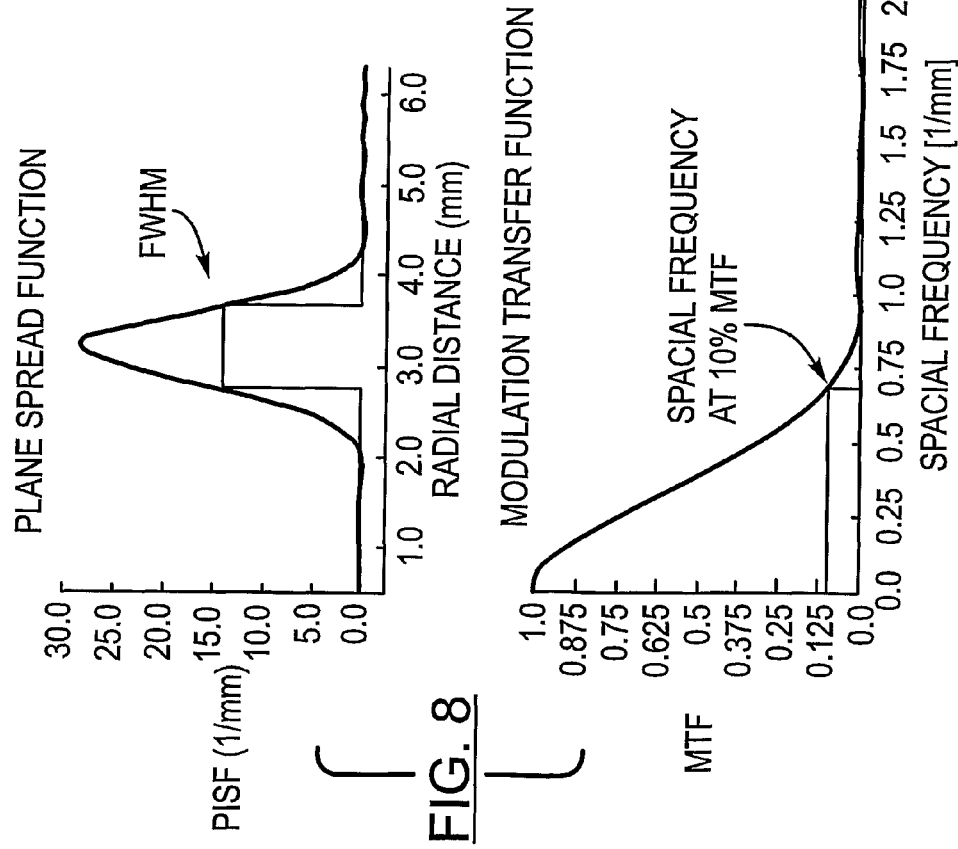
FIG. 8 shows a resulting plane spread function (PISF) from which full width at half maximum (FWHM) is measured and a derived modulated full width at half maximum (MTF) identifying the limiting spatial frequency.

FIG. 6 shows an image slice through a reconstructed volumetric image of the image phantom together with a profile line plot taken through the image slice. FIG. 7 shows the resulting SSF curve derived from the profile line plot of FIG. 6. FIG. 8 shows the resulting PISF curve from which the FWHM is measured together with the derived MTF identifying the limiting spatial frequency of the CT scanner.

Precision measurements were made for the GE VCT only. The variability of measurement of FWHM and 10% MTF was higher for axial (superior-inferior) measurements than trans-axial (left-right, anterior-posterior) measurements. This is likely due to the fact that fewer points are used to assemble the axial SSF curves and therefore there is less noise averaging in the binning procedure as compared to the formation of the trans-axial SSF curves. The respective mean values and standard deviations for the GE VCT are shown in Table 2 below.

TABLE 2

| | FWHM [mm] | | 10% MTF [lp/mm] | |
|---|---|---|---|---|
| | trans-axial | axial | trans-axial | axial |
| mean (n = 5) | 1.101 | 0.617 | 0.725 | 1.335 |
| std dev | 0.011 | 0.033 | 0.000 | 0.084 |

The variation in measurement of resolution as a function of sphere size is shown in Table 3 below for sphere diameters of 0.5 inch, 1 inch and 1.5 inches, for both the GE VCT and SMS 64.

TABLE 3

TRANSVERSE

|  | FWHM [mm] | | 10% MTF [lp/mm] | |
| --- | --- | --- | --- | --- |
| Ball dia. | GE VCT | SMS 64 | GE VCT | SMS 64 |
| 0.5" | 1.157 | 1.210 | 0.750 | 0.700 |
| 1" | 1.094 | 1.170 | 0.725 | 0.700 |
| 1.5" | 1.094 | 1.210 | 0.725 | 0.675 |
| mean | 1.115 | 1.197 | 0.733 | 0.692 |
| std dev | 0.036 | 0.023 | 0.014 | 0.014 |

AXIAL

|  | FWHM [mm] | | 10% MTF [lp/mm] | |
| --- | --- | --- | --- | --- |
| Ball size | GE VCT | SMS 64 | GE VCT | SMS 64 |
| 0.5" | 1.055 | 0.703 | 0.800 | 1.200 |
| 1" | 0.976 | 0.781 | 0.800 | 1.050 |
| 1.5" | 1.015 | 0.781 | 0.800 | 1.050 |
| mean | 1.015 | 0.755 | 0.800 | 1.100 |
| std dev | 0.040 | 0.045 | 0.000* | 0.087 |

*Note: The sampling interval of the MTF was 0.025 lp/mm. The 0.000 std dev. is a result of quantization.

The variation in measurements of resolution as a function of sphere size is shown in the Table 4 below for sphere diameters of 0.5 inch, 1 inch and 1.5 inches, for the GE VCT.

TABLE 4

| gantry | | FWHM [mm] | | | MTF@10% [lp/mm] | | |
| --- | --- | --- | --- | --- | --- | --- | --- |
| speed | location | RL | AP | SI | RL | AP | SI |
| 1.0 sec | iso-centre | 1.094 | 1.094 | 0.585 | 0.725 | 0.725 | 1.350 |
| 1.0 sec | 180 mm | 1.250 | 1.480 | 0.898 | 0.650 | 0.550 | 0.875 |
| 0.4 sec | 180 mm | 1.250 | 1.480 | 0.898 | 0.650 | 0.550 | 0.875 |

Table 5 below compares the FWHM and the 10% MTF spatial frequency for protocols with no table motion during scanning (axial) and a table speed of 20 mm/sec (spiral).

TABLE 5

|  | FWHM [mm] | | 10% MTF [lp/mm] | |
| --- | --- | --- | --- | --- |
| system/mode | trans-axial | axial | trans-axial | axial |
| GE VCT axial* | 1.100 | 0.617 | 0.725 | 1.335 |
| GE VCT spiral | 1.090 | 0.976 | 0.725 | 0.800 |
| SMS 64 axial* | 1.130 | 1.050 | 0.760 | 0.700 |
| SMS 64 spiral | 1.190 | 0.760 | 0.750 | 1.050 |

Those of skill in the art will appreciate that the described resolution evaluation method may be applied to other volumetric imaging modalities such as for example magnetic resonance imaging, ultrasound, optical, SPECT and PET imaging.

Although a preferred embodiment has been described with reference to the accompanying drawings, those of skill in the art will appreciate that variations and modifications may be made without departing from the spirit and scope thereof as defined by the appended claims.

What is claimed is:

1. A method of evaluating axial and trans-axial resolution of a scanner of a volumetric imaging system, comprising:
   placing an image phantom comprising a high contrast sphere in a uniform medium within a field of view of said scanner;
   scanning the image phantom using the scanner and generating resultant volumetric image data (voxels);
   identifying a first conic region having a vertex generally coincident with the sphere centroid, said first conic region being centered about a positive axis of the scanning geometry of the scanner and identifying a second conic region having a vertex generally coincident with the sphere centroid, said second conic region being centered about a negative axis of the scanning geometry;
   processing voxels within the first and second conic regions to assemble surface spread curves in positive and negative axial directions;
   processing voxels outside of the first and second conic regions to assemble surface spread curves in positive and negative trans-axial directions; and
   processing the surface spread curves in the positive and negative axial and trans-axial directions to yield a modulation transfer function representing the axial and trans-axial resolution of said scanner.

2. The method of claim 1, wherein the diameter of said sphere is at least three times a spacing of said resultant voxels.

3. The method of claim 1, wherein said uniform medium is an acrylic plastic.

4. The method of claim 1, wherein said uniform medium is air and wherein said sphere is supported by structural elements.

5. The method of claim 1, wherein said sphere has an attenuation coefficient that is at least three times an attenuation coefficient of said uniform medium.

6. The method of claim 1, wherein during said scanning, the image phantom and said scanner are rotated relative to one another transverse to the plane of rotation.

7. The method of claim 1, wherein during said scanning, said sphere is placed at a plurality of locations along a radial axis within said uniform medium.

8. The method of claim 1, wherein during scanning, said image phantom is placed at different positions along a radial axis of the field of view of said scanner.

9. The method of claim 1 wherein said first and second conic regions are of generally equal volumes.

10. The method of claim 9 wherein said first conic region is defined by a ray subtending a 30 degree angle with respect to said positive axis and rotated about said positive axis and wherein said second conic region is defined by a ray subtending a 30 degree angle with respect to said negative axis and rotated about said negative axis.

11. The method of claim 9 further comprising:
   using the modulation transfer function to determine the directionally dependant resolution of the scanner during display of an image; and
   presenting a graphical representation of the directionally dependant resolution corresponding to the orientation of the image being viewed.

12. The method of claim 1 wherein said sphere is encased in a solid cylinder.

13. The method of claim 11 wherein said sphere is formed of Teflon™ and said cylinder is formed of silicone.

14. A method of evaluating axial and trans-axial resolution of a scanner of a volumetric imaging system, comprising:

placing an image phantom comprising a high contrast sphere in a uniform medium within the field of view of said scanner;

scanning the image phantom using the scanner and generating resultant volumetric image data (voxels);

identifying a first conic region having a vertex generally coincident with the sphere centroid, said first conic region being centered about a positive axis of the scanning geometry of the scanner and identifying a second conic region having a vertex generally coincident with the sphere centroid, said second conic region being centered about a negative axis of the scanning geometry;

processing voxels within the first and second conic regions to assemble surface spread curves in positive and negative axial directions;

identifying a third conic region having a vertex generally coincident with the sphere centroid, said third conic region being centered about the positive axis of the scanning geometry of the scanner and identifying a fourth conic region having a vertex generally coincident with the sphere centroid, said fourth conic region being centered about a negative axis of the scanning geometry, said third and fourth conic regions encompassing greater volumes than said first and second conic regions;

processing voxels outside of the third and fourth conic regions to assemble surface spread curves in positive and negative trans-axial directions; and processing the surface spread curves in the positive and negative axial and trans-axial directions to yield a modulation transfer function representing the axial and trans-axial resolution of said scanner.

15. The method of claim 14 wherein said first and second conic regions are of generally equal volumes and wherein said third and fourth conic regions are of generally equal volumes.

16. The method of claim 15 wherein said first conic region is defined by a ray subtending a 30 degree angle with respect to said positive axis and rotated about said positive axis and wherein said second conic region is defined by a ray subtending a 30 degree angle with respect to said negative axis and rotated about said negative axis.

17. The method of claim 15 wherein said third conic region is defined by a ray subtending a 60 degree angle with respect to said positive axis and rotated about said positive axis and wherein said fourth conic region is defined by a ray subtending a 60 degree angle with respect to said negative axis and rotated about said negative axis.

18. The method of claim 15 wherein said first conic region is defined by a ray subtending a 30 degree angle with respect to said positive axis and rotated about said positive axis, wherein said second conic region is defined by a ray subtending a 30 degree angle with respect to said negative axis and rotated about said negative axis, wherein said third conic region is defined by a ray subtending a 60 degree angle with respect to said positive axis and rotated about said positive axis and wherein said fourth conic region is defined by a ray subtending a 60 degree angle with respect to said negative axis and rotated about said negative axis.

19. The method of claim 15 wherein during processing of voxels outside of the third and fourth conic regions, voxels within a region defined by a union of anti-conic regions outside of the third and fourth conic regions and above and below a plane transverse to said positive and negative axes intersecting the sphere centroid are processed.

20. The method of claim 19 wherein said region is divided into quadrants prior to processing of said voxels and wherein the voxels in each quadrant are processed separately.

21. The method of claim 19, wherein the diameter of said sphere is at least three times a spacing of said resultant voxels.

22. The method of claim 19, wherein said uniform medium is an acrylic plastic.

23. The method of claim 19, wherein said uniform medium is air and wherein said sphere is supported by structural elements.

24. The method of claim 19, wherein said sphere has an attenuation coefficient that is at least three times an attenuation coefficient of said uniform medium.

25. The method of claim 19, wherein during said scanning, the image phantom and said scanner are rotated relative to one another transverse to the plane of rotation.

26. The method of claim 19, wherein during said scanning, said sphere is placed at a plurality of locations along a radial axis within said uniform medium.

27. The method of claim 19, wherein during scanning, said image phantom is placed at different positions along a radial axis of the field of view of said scanner.

28. The method of claim 19 further comprising:
using the modulation transfer function to determine the directionally dependant resolution of the scanner during display of an image; and
presenting a graphical representation of the directionally dependant resolution corresponding to the orientation of the image being viewed.

29. The method of claim 19 wherein said sphere is encased in a solid cylinder.

* * * * *